(12) United States Patent
Levy et al.

(10) Patent No.: US 10,155,093 B2
(45) Date of Patent: Dec. 18, 2018

(54) APPARATUS AND METHOD FOR PRODUCING $CO_2$ ENRICHED MEDICAL FOAM

(71) Applicants: Frank Levy, Fort Myers, FL (US); Kimberley Levy, Fort Myers, FL (US)

(72) Inventors: Frank Levy, Fort Myers, FL (US); Kimberley Levy, Fort Myers, FL (US)

( * ) Notice: Subject to any disclaimer, the term of this patent is extended or adjusted under 35 U.S.C. 154(b) by 297 days.

(21) Appl. No.: 15/053,530

(22) Filed: Feb. 25, 2016

(65) Prior Publication Data

US 2016/0166782 A1 Jun. 16, 2016

Related U.S. Application Data

(63) Continuation-in-part of application No. 14/509,459, filed on Oct. 8, 2014, now Pat. No. 9,744,342, which
(Continued)

(51) Int. Cl.
*A61M 13/00* (2006.01)
*A61M 5/20* (2006.01)
(Continued)

(52) U.S. Cl.
CPC ......... *A61M 13/003* (2013.01); *A61K 9/0019* (2013.01); *A61K 9/122* (2013.01); *A61L 31/146* (2013.01); *A61L 31/16* (2013.01); *A61M 5/2053* (2013.01); *A61M 35/00* (2013.01); *A61M 35/003* (2013.01); *A61M 37/00* (2013.01); *A61B 17/12186* (2013.01); *A61B 2017/00778* (2013.01); *A61B 2017/00884* (2013.01);
(Continued)

(58) Field of Classification Search
CPC .. A61M 13/003; A61M 5/2053; A61M 35/00; A61M 35/003; A61M 37/00; A61L 31/146; A61K 9/122
USPC .......................................................... 604/24
See application file for complete search history.

(56) References Cited

U.S. PATENT DOCUMENTS

| 2,475,511 A | 7/1949 | Nicholson |
| 2,631,321 A | 3/1953 | Mureau |

(Continued)

FOREIGN PATENT DOCUMENTS

| CN | 2179152 Y | 10/1994 |
| DE | 10161027 A1 | 6/2003 |

(Continued)

*Primary Examiner* — Edelmira Bosques
(74) *Attorney, Agent, or Firm* — Welsh Flaxman & Gitler LLC

(57) ABSTRACT

A gas enriched foam generating apparatus for performing medical procedures includes a foam generating tip assembly composed of a multi-channel arrangement at a proximal first end thereof and a tip at a distal second end thereof. The apparatus also includes a compressed gas unit fluidly connected to the multi-channel arrangement at a proximal first end of the foam generating tip assembly and a medical solution fluidly connected to the multi-channel arrangement at a proximal first end of the foam generating tip assembly. Compressed gas, from the compressed gas unit, and the medical solution are combined within the foam generating tip assembly in a manner generating a gas enriched foam that is ultimately dispensed from the foam generating apparatus.

30 Claims, 12 Drawing Sheets

Related U.S. Application Data is a continuation of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760.

(60) Provisional application No. 62/121,827, filed on Feb. 27, 2015, provisional application No. 60/867,323, filed on Nov. 27, 2006.

(51) Int. Cl.
| | | |
|---|---|---|
| *A61M 35/00* | (2006.01) | |
| *A61M 37/00* | (2006.01) | |
| *A61L 31/14* | (2006.01) | |
| *A61L 31/16* | (2006.01) | |
| *A61K 9/00* | (2006.01) | |
| *A61K 9/12* | (2006.01) | |
| *A61B 17/00* | (2006.01) | |
| *A61B 17/12* | (2006.01) | |

(52) U.S. Cl.
CPC ..... *A61B 2017/00893* (2013.01); *A61K 9/124* (2013.01); *A61L 2300/418* (2013.01); *A61L 2430/36* (2013.01); *A61M 2210/12* (2013.01)

(56) References Cited

U.S. PATENT DOCUMENTS

| | | |
|---|---|---|
| 2,688,428 A | 9/1954 | Manhartsberger |
| 2,789,304 A | 4/1957 | Leavin |
| 2,828,889 A | 4/1958 | Joschko |
| 3,004,686 A | 10/1961 | McKee |
| 3,034,332 A | 5/1962 | Lederer |
| 3,268,939 A | 8/1966 | Aversa |
| 3,426,768 A | 2/1969 | Vardaros |
| 3,831,844 A | 8/1974 | Tropeano et al. |
| 3,879,703 A | 4/1975 | Bonazoli et al. |
| 4,135,269 A | 1/1979 | Marston |
| 4,189,068 A | 2/1980 | Apellaniz |
| 4,219,021 A | 8/1980 | Fink |
| 4,567,905 A | 2/1986 | Stewart et al. |
| 4,596,261 A | 6/1986 | Renda et al. |
| 4,744,356 A | 5/1988 | Greenwood |
| 4,786,394 A | 11/1988 | Enzer et al. |
| 4,950,230 A | 8/1990 | Kendell |
| 5,109,877 A | 5/1992 | Takeda |
| 5,135,026 A | 8/1992 | Manska |
| 5,154,348 A | 10/1992 | Ratnik et al. |
| 5,195,963 A | 3/1993 | Yafuso et al. |
| 5,246,140 A | 9/1993 | Thix et al. |
| 5,345,932 A | 9/1994 | Yafuso et al. |
| 5,395,318 A | 3/1995 | Kaprelian |
| 5,580,530 A | 12/1996 | Kowatsch et al. |
| 5,699,961 A | 12/1997 | Ratnik et al. |
| 5,815,877 A | 10/1998 | Haneveld |
| D401,419 S | 11/1998 | Hartmann et al. |
| 5,926,903 A | 7/1999 | Kim |
| 6,070,594 A | 6/2000 | Mears |
| 6,070,597 A | 6/2000 | Motherhead |
| 6,164,556 A | 12/2000 | Dupre et al. |
| 6,192,883 B1 | 2/2001 | Miller, Jr. |
| 6,295,007 B1 | 9/2001 | O'Meara |
| 6,315,762 B1 | 11/2001 | Recinella et al. |
| 6,378,570 B1 | 4/2002 | Shipachev et al. |
| 6,402,047 B1 | 6/2002 | Thomas |
| 6,461,568 B1 | 10/2002 | Eckhardt |
| 6,474,091 B2 | 11/2002 | Guerra |
| 6,572,873 B1 | 6/2003 | Osman et al. |
| 6,895,624 B2 | 5/2005 | Fischer et al. |
| 6,997,321 B2 | 2/2006 | Young |
| 7,162,802 B2 | 1/2007 | Barnardeau et al. |
| 7,543,760 B2 | 6/2009 | Levy et al. |
| 7,918,620 B2 | 4/2011 | Del Ponte |
| 8,074,666 B2 | 12/2011 | Piao |
| 8,132,285 B2 | 3/2012 | Piao |
| 9,011,031 B2 | 4/2015 | Piao |
| 2001/0044618 A1 | 11/2001 | Recinella et al. |
| 2002/0017328 A1 | 2/2002 | Loo |
| 2002/0174578 A1 | 11/2002 | Ross |
| 2003/0034459 A1 | 2/2003 | Bonin |
| 2003/0082243 A1* | 5/2003 | Harman ............... A61K 9/0019 424/600 |
| 2003/0181850 A1 | 9/2003 | Diamond et al. |
| 2004/0168700 A1 | 9/2004 | Dorf |
| 2005/0000981 A1 | 1/2005 | Peng et al. |
| 2005/0092315 A1 | 5/2005 | Bachelder |
| 2005/0103342 A1 | 5/2005 | Jorczak et al. |
| 2005/0119607 A1 | 6/2005 | Van Der Linden et al. |
| 2006/0004322 A1 | 1/2006 | Uesugi et al. |
| 2006/0071091 A1 | 4/2006 | Ratnik |
| 2006/0074386 A1 | 4/2006 | Wollmann |
| 2006/0175554 A1 | 8/2006 | Riddell |
| 2006/0178620 A1 | 8/2006 | Wollmann |
| 2007/0104616 A1 | 5/2007 | Keenan et al. |
| 2007/0111298 A1 | 5/2007 | Muller et al. |
| 2008/0004549 A1 | 1/2008 | Anderson et al. |
| 2008/0120992 A1 | 5/2008 | Levy et al. |
| 2008/0167621 A1 | 7/2008 | Wagner et al. |
| 2009/0062741 A1 | 3/2009 | Smith et al. |
| 2009/0318890 A1 | 12/2009 | Levy |
| 2010/0101579 A1 | 4/2010 | Levy |
| 2011/0112041 A1 | 5/2011 | Schiffmann |
| 2011/0218411 A1 | 9/2011 | Keenan et al. |

FOREIGN PATENT DOCUMENTS

| | | |
|---|---|---|
| EP | 2468204 A1 | 6/2012 |
| WO | WO00/72821 | 12/2000 |
| WO | WO02/41872 | 5/2002 |
| WO | WO2005/048984 | 6/2005 |

* cited by examiner

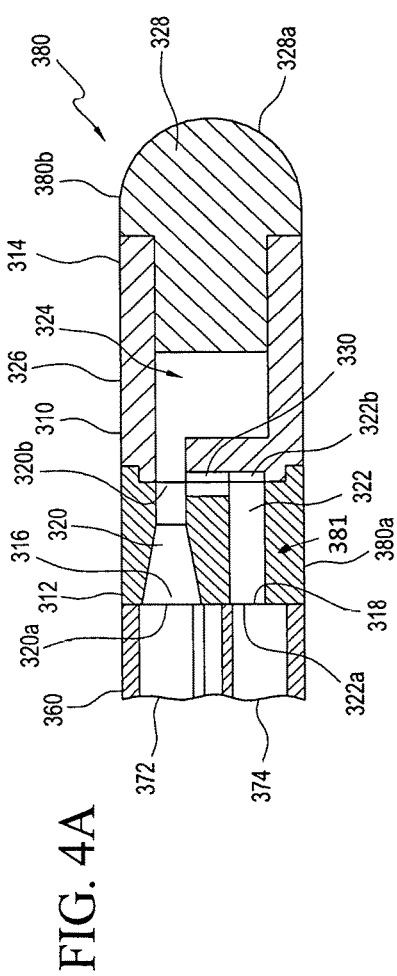
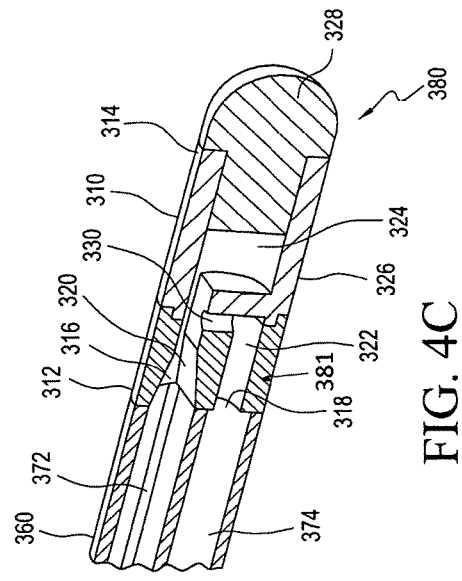
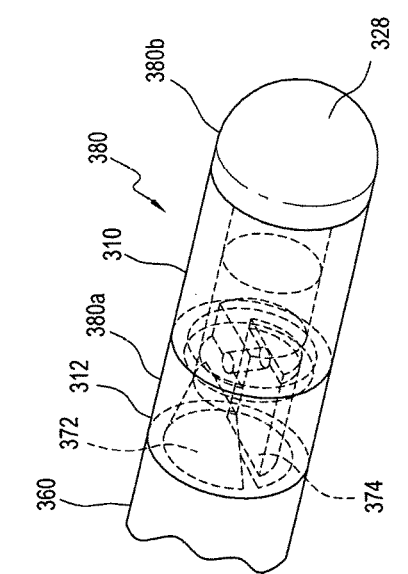
FIG. 4A
FIG. 4C
FIG. 4B

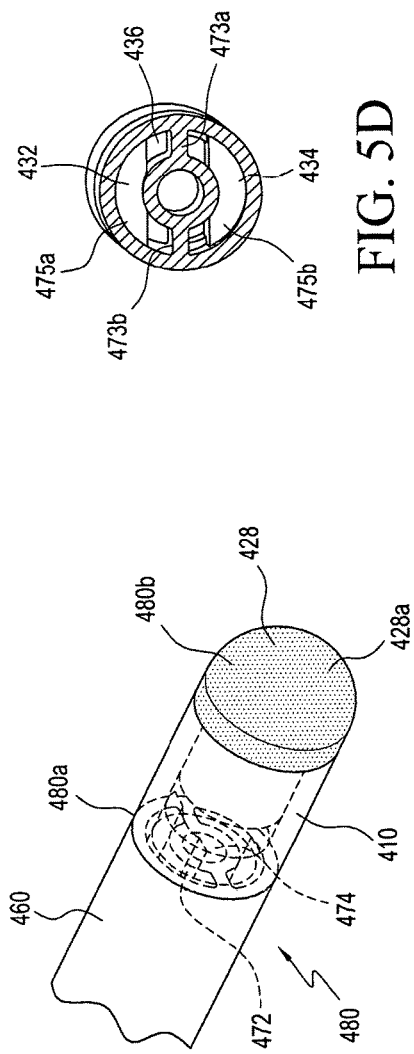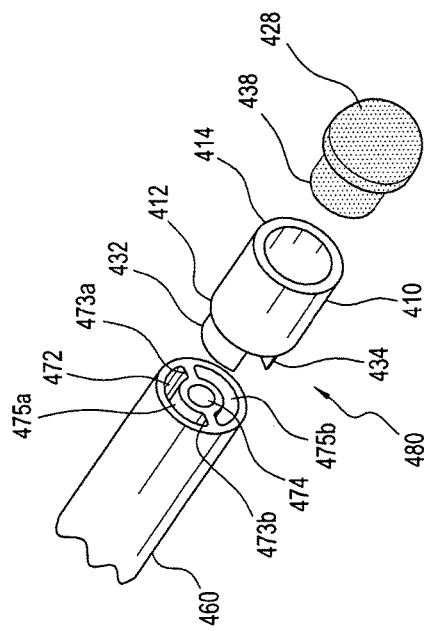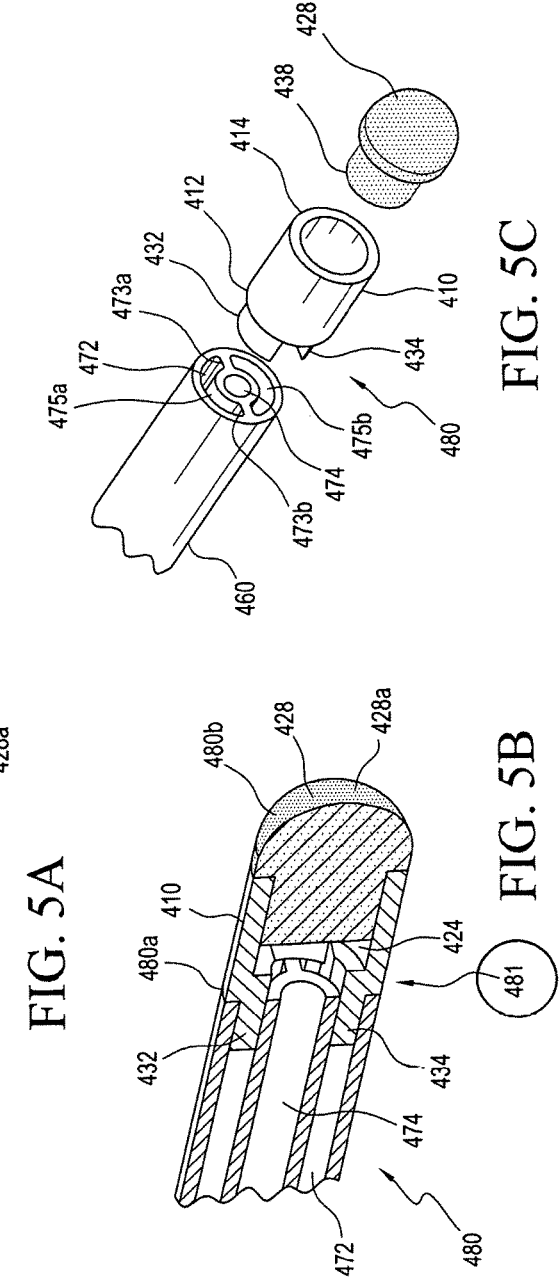

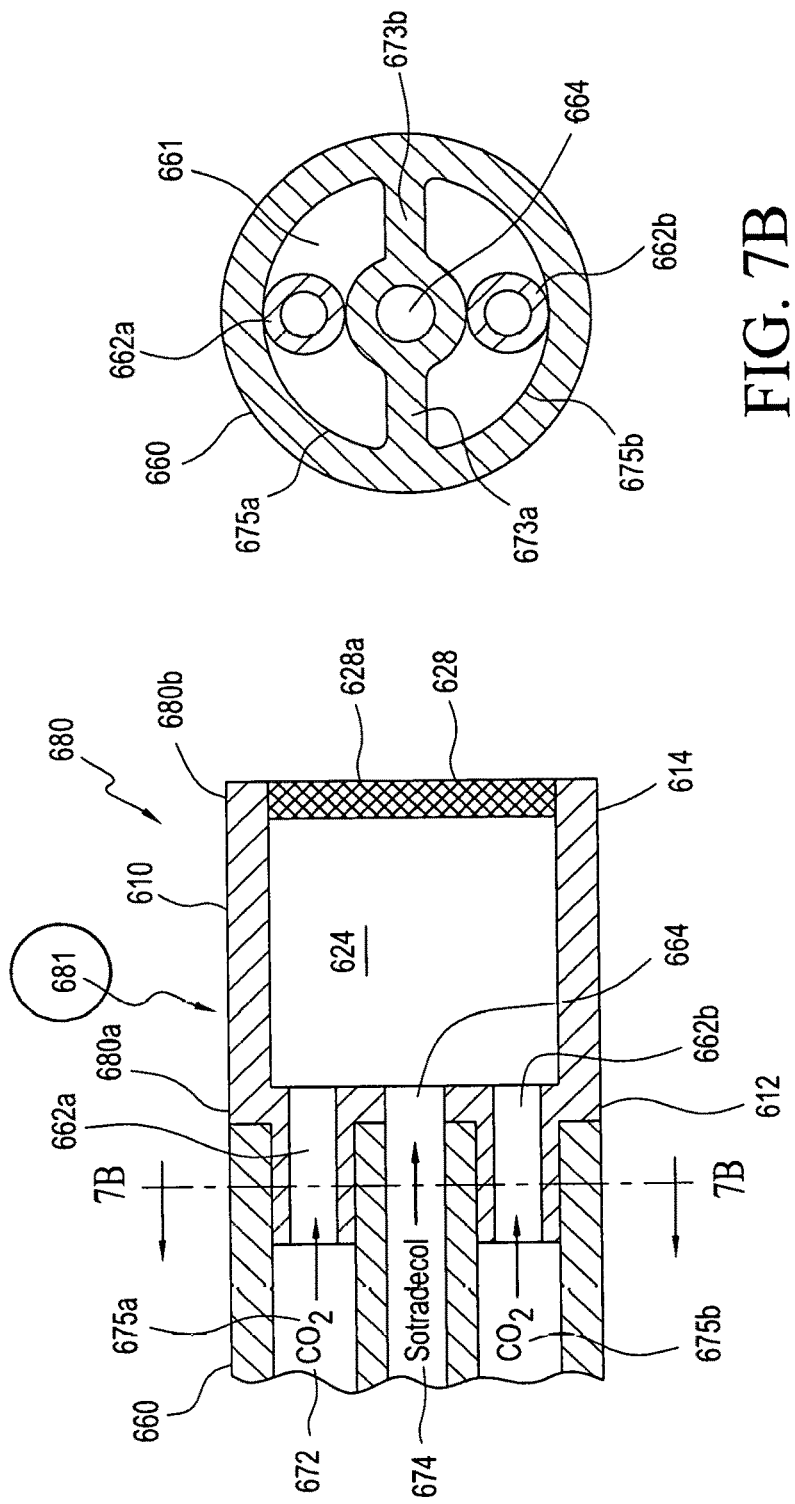

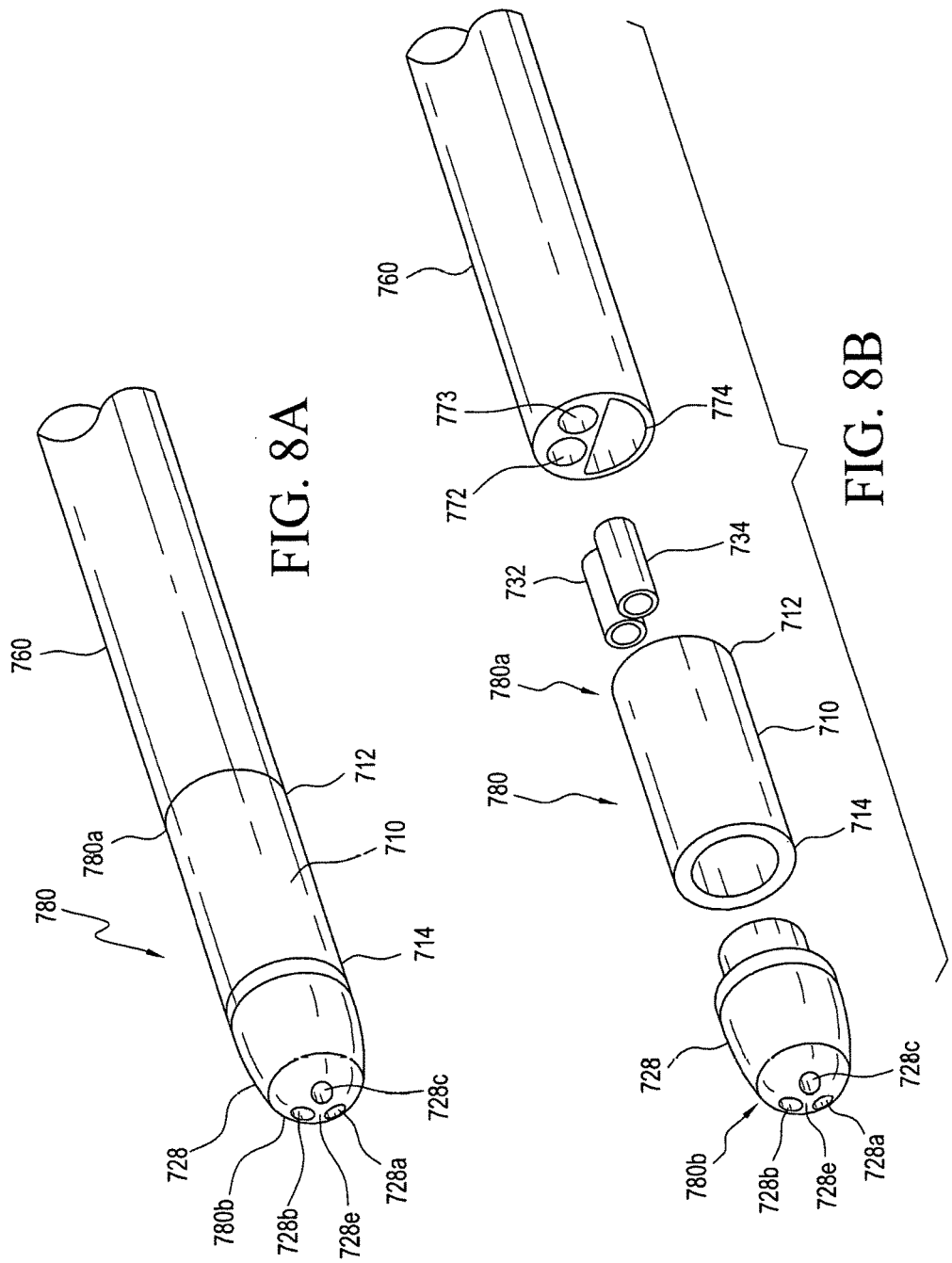

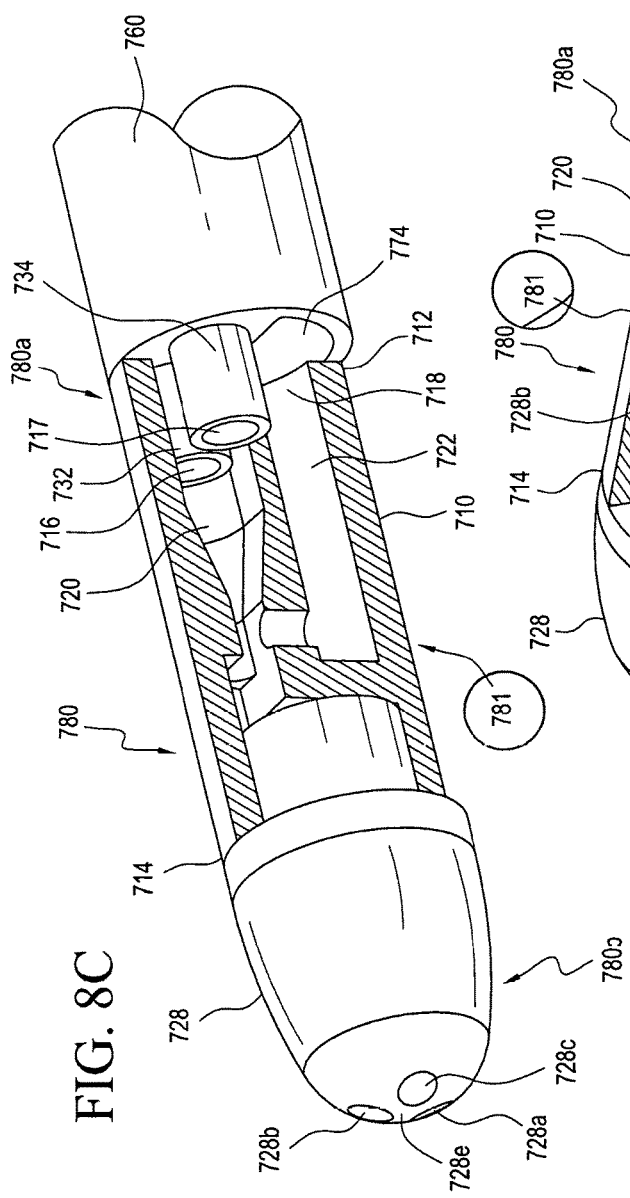
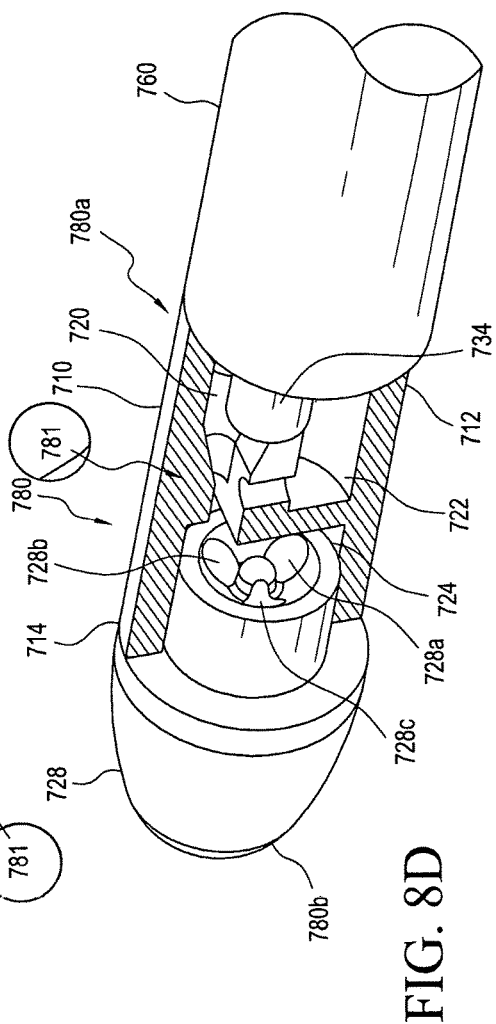
FIG. 8C
FIG. 8D

APPARATUS AND METHOD FOR PRODUCING $CO_2$ ENRICHED MEDICAL FOAM

CROSS REFERENCE TO RELATED APPLICATION

This application claims the benefit of U.S. Provisional Patent Application Ser. No. 62/121,827, entitled "CATHETER FOR PRODUCING $CO_2$ ENRICHED MEDICAL FOAM," filed Feb. 27, 2015, and this application is a continuation-in-part of U.S. patent application Ser. No. 14/509,459, filed Oct. 8, 2014, which is currently pending, which is a continuation of U.S. patent application Ser. No. 13/068,680, filed May 17, 2011, which is now U.S. Pat. No. 8,876,749, which is a continuation-in-part of U.S. patent application Ser. No. 12/652,845 filed Jan. 6, 2010, which is abandoned, which is a continuation-in-part of U.S. patent application Ser. No. 12/210,368 filed Sep. 15, 2008, which is abandoned, which is a continuation-in-part of U.S. patent application Ser. No. 11/945,674 filed Nov. 27, 2007, which is U.S. Pat. No. 7,543,760, which claims the benefit of U.S. Provisional Patent Application Ser. No. 60/867,323 filed Nov. 27, 2006, the disclosures of which are incorporated herein by reference in their entirety.

BACKGROUND OF THE INVENTION

1. Field of the Invention

This invention relates to an apparatus and process for producing $CO_2$ enriched medical foam.

2. Description of the Related Art

The present invention utilizes the Venturi effect to produce medical grade foam comprising $CO_2$ for use in various applications. The apparatus of the present invention is simple to manufacture and use because it does not require an impeller and incorporated fan with a foam generator in order to create and dispense the foam.

The Venturi effect is an example of Bernoulli's principle, in the case of incompressible fluid flow through a tube or pipe with a constriction in it. The fluid velocity must increase through the constriction to satisfy the equation of continuity, while its pressure must decrease due to conservation of energy; the gain in kinetic energy is supplied by a drop in pressure or a pressure gradient force.

The limiting case of the Venturi effect is choked flow, in which a constriction in a pipe or channel limits the total flow rate through the channel because the pressure cannot drop below zero in the constriction. Choked flow is used to control the delivery rate of water and other fluids through spigots and other types of valves. The portable apparatus of the present invention utilizes a source of compressed gas, namely $CO_2$, to produce the desired pressure and airflow for the effective creation of medical foam.

SUMMARY OF THE INVENTION

The present invention provides for a novel apparatus for producing medical foam as well as a process for utilizing such foam in medical treatment, in particular, sclerotherapy. One embodiment of the present invention features an apparatus for producing and delivering medical foam comprising (i) a foam generating catheter including a syringe containing a medical agent (in particular, a sclerosing agent), a dual lumen catheter and a foam generating tip assembly; and (ii) a compressed gas unit having at least one container of compressed gas and the gas regulator valve.

The compressed gas is any suitable compressed gas. Suitable compressed gases may preferably include carbon dioxide and atmospheric air or mixtures thereof. The compressed gas is contained in one or more compressed gas containers. The apparatus has a source of electric power that may be delivered by batteries providing between about 3-24 volts. The apparatus also has a foam generating tip that includes a porous membrane or other porous material providing a surface for the formation of medial foam. In a preferred embodiment, the gas regulator valve is an electronically activated solenoid or a pressure activated valve. Additionally preferred, the gas regulator valve may be an electronically activated solenoid controlled by a pressure activation switch or actuator, wherein the pressure switch activates the solenoid when depressed.

In another embodiment, the apparatus of the present invention includes compressed gas storage, with a hose or other acceptable transport mechanism to deliver the compressed gas to the foam generating tip assembly or any other receptacle, which forms part of either a catheter or needle. The foam generating tip assembly includes a novel arrangement by which compressed gas enters a second end of the foam generating tip assembly through a gas inlet. The resultant pressure produced within the foam generating tip assembly draws medical solution into the interior of the foam generating tip assembly through a second inlet. The compressed gas continues to travel towards the first end of the foam generating tip assembly onto which the porous membrane or other porous material is affixed. The porous membrane or other porous material provides a surface at which the medical solution mixes with the compressed gas and the medical solution foams. The compressed gas passes through the porous membrane or other porous material, and lifts the foams off the porous membrane or other porous material outward from the foam generating tip assembly. Thus, the solution, now foamed by the compressed gas, can be delivered and applied.

In another embodiment, a user will utilize two separate units of the apparatus wherein a first unit includes at least one compressed gas cylinder and a valve for controlling the release of compressed gas from the cylinder. In one embodiment, the valve for controlling the release of compressed gas is an electronic solenoid.

The present invention also relates to methods of medical treatments. In one embodiment the invention is a method for providing $CO_2$ enriched foam and applying such foam to the vascular system comprising the steps of: (i) providing a portable $CO_2$ apparatus; (ii) providing a container (for example, a syringe) with a medical solution in the form of a sclerosing agent, the container having an entrance, an exit and a release means regulating the exit; (iii) attaching a medically acceptable directional device from the apparatus to the entrance of the container; (iv) initiating an actuator of the apparatus to release $CO_2$; (v) activating the release mechanism to produce a medical foam containing $CO_2$; and (vi) applying the medical foam to a predetermined vascular location via a catheter or needle. In medical uses, $CO_2$ is used because it is safer and has fewer complications than air or oxygen in the same uses. $CO_2$ diffuses more naturally in body tissues and is absorbed in the body more rapidly and with fewer side effects. The present invention can deliver $CO_2$ from an adjustable port that controls the psi from 0 psi to 120 psi.

Previous methods utilizing large $CO_2$ tanks and regulators are dangerous because of the risk of a seal, valve, or part malfunction causing a projectile in a medical setting and the potential for explosive delivery. The present invention is safer as it eliminates these possibilities of malfunction.

The present invention requires very little space to store, as opposed to the cumbersome existing tank systems and is much easier to use, with a push button actuator to initiate operation. The present invention is much less expensive than current $CO_2$ tank systems. Acquisition of the $CO_2$ in the present invention now requires only cartridges which can be delivered in a small box. The current tanks require filling at a filling station which involves the transport of a large quantity of $CO_2$ which is ultimately inconvenient.

With the foregoing in mind, it is an object of the present invention to provide a gas enriched foam generating apparatus for performing medical procedures. The apparatus includes a foam generating tip assembly composed of a multi-channel arrangement at a proximal first end thereof and a tip at a distal second end thereof. The apparatus also includes a compressed gas unit fluidly connected to the multi-channel arrangement at a proximal first end of the foam generating tip assembly and a medical solution fluidly connected to the multi-channel arrangement at a proximal first end of the foam generating tip assembly. Compressed gas, from the compressed gas unit, and the medical solution are combined within the foam generating tip assembly in a manner generating a gas enriched foam that is ultimately dispensed from the foam generating apparatus.

It is also an object of the present invention to provide a foam generating apparatus including a dual lumen catheter including a first end and a second end to which the foam generating tip assembly is secured.

It is another object of the present invention to provide a foam generating apparatus wherein the compressed gas unit is fluidly connected to a first lumen of the dual lumen catheter.

It is a further object of the present invention to provide a foam generating apparatus wherein the medical solution is fluidly connected to a second lumen of the dual lumen catheter.

It is another object of the present invention to provide a foam generating apparatus wherein the multi-channel arrangement of the foam generating tip assembly employs a Venturi arrangement with a mixing chamber.

It is also an object of the present invention to provide a foam generating apparatus wherein the tip member is composed of a sintered material having a porous structure allowing for the passage of the pressurized gas and the medical solution.

It is a further object of the present invention to provide a foam generating apparatus wherein the foam generating tip assembly includes a tip member composed of a sintered material having a porous structure allowing for the passage of the pressurized gas and the medical solution.

It is another object of the present invention to provide a foam generating apparatus wherein the compressed gas is pressurized $CO_2$.

It is also an object of the present invention to provide a foam generating apparatus wherein the medical solution is a sclerosing agent.

It is a further object of the present invention to provide a medical method for treating arteries using the foam generating apparatus.

It is another object of the present invention to provide a medical method for treating veins using the foam generating apparatus.

It is another object of the present invention to provide a medical method wherein the vein is the great saphenous vein.

It is another object of the present invention to provide a foam generating apparatus with a needle body including the foam generating tip assembly.

It is another object of the present invention to provide a foam generating apparatus wherein the compressed gas unit and the medical solution are fluidly connected to the multi-channel arrangement at a needle hub at the proximal end of the needle body.

It is another object of the present invention to provide a foam generating apparatus the multi-channel arrangement of the foam generating tip assembly employs a Venturi arrangement with a mixing chamber.

It is another object of the present invention to provide a foam generating apparatus wherein the tip member is composed of a material having a porous structure allowing for the passage of the pressurized gas and the medical solution.

Other objects and advantages of the present invention will become apparent from the following detailed description when viewed in conjunction with the accompanying drawings, which set forth certain embodiments of the invention.

BRIEF DESCRIPTION OF THE DRAWINGS

Other objects, features and advantages will occur from the following description of a preferred embodiment and the accompanying drawings.

FIGS. 4A, 4B and 4C respectively show a longitudinal cross sectional view, a perspective view and a perspective cross sectional view of a foam generating tip assembly in accordance with an alternate first embodiment.

FIGS. 5A, 5B, 5C and 5D are respectively a perspective view, a longitudinal cross-sectional perspective view, an exploded view and a lateral cross-sectional view of a foam generating tip assembly in accordance with an alternate second embodiment.

FIGS. 7A and 7B are respectively a longitudinal cross-sectional view and a lateral cross-sectional view of a foam generating tip assembly in accordance with an alternate fourth embodiment;

FIGS. 8A, 8B, 8C, 8D and 8E are respectively a perspective view, an exploded view, a front partial cross-sectional view, a rear partial cross-sectional view and a lateral cross-sectional view in accordance with a fifth embodiment;

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
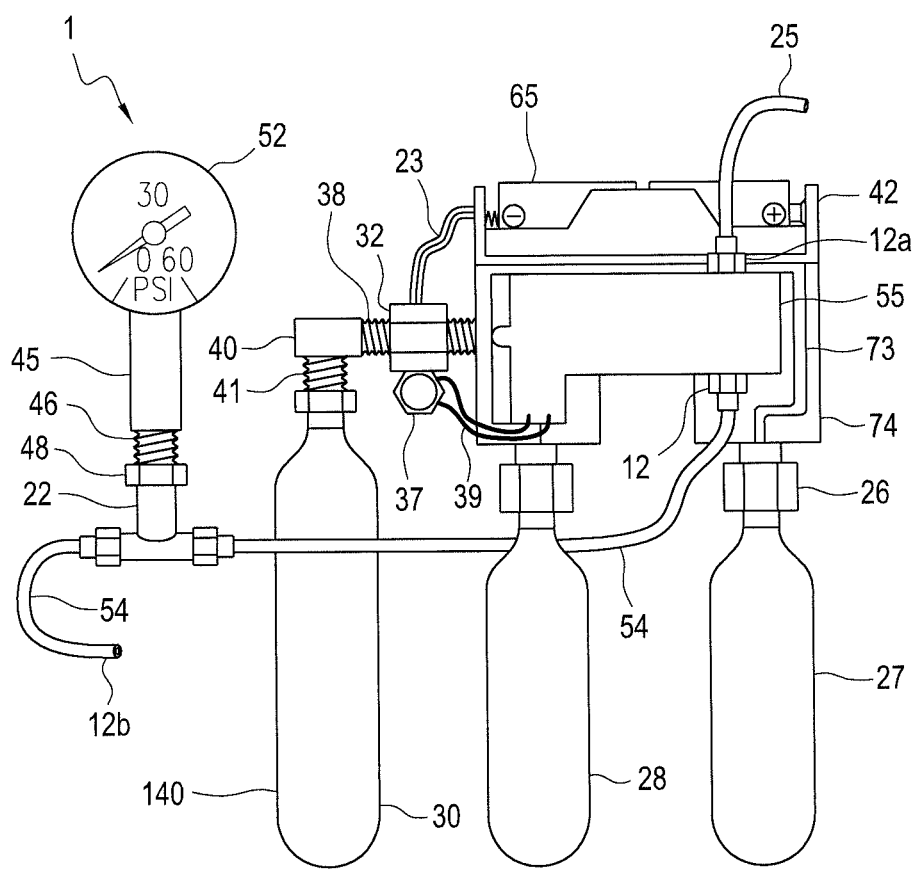
FIG. 1 is a side perspective and partly schematic view of an apparatus including compressed gas ($CO_2$) cylinders and a solenoid of the present invention.

In FIG. 1 a compressed gas unit 1 comprises a solenoid 55 with at least one compressed gas ($CO_2$) cylinder 27. In one embodiment, the compressed gas cylinder 27 is 25 g or larger. The compressed gas cylinder 27 is secured into position to the compressed gas unit 1 by means of a cylinder cartridge puncture valve 26 and a fitting 74. In a preferred embodiment, the cylinder cartridge puncture valve 26 has a mechanism for piercing the compressed gas cylinder 27, as is known, and holding or securing the cylinder 27 in place. Compressed gas is delivered to the solenoid 55 from the compressed gas cylinder 27 through the cylinder cartridge puncture valve 26 and a channel 73 of the fitting 74. The compressed gas unit 1 has at least one battery 65, held in place by a battery holder 42, for providing electrical power by which the solenoid 55 may be activated and then regulated by a pressure activation switch or actuator 37. The battery 65 supplies power to the solenoid 55 through a switch wire assembly 23, which is connected to the activation switch 37. The activation switch 37 is mounted to a pressure nut 32 carried on a threaded conduit 38. The compressed gas unit 1 has electrical wiring 39 for providing necessary electricity from activation switch 37 to the solenoid 55. The compressed gas unit 1 also comprises a black rock regulator 140, which is controlled by a secondary regulator adjustment knob 30 when the solenoid 55 is activated. The black rock regulator 140 is communicably connected to a compressed gas unit 1 by an elbow pipe 40. The elbow pipe 40 includes a threaded vertical conduit segment 41 joined to the regulator 140 through a connector nut and a threaded horizontal conduit 38, which is engaged by the pressure nut 32.

The compressed gas cylinder 27 is secured to the compressed gas unit 1 by the cartridge puncture valve 26 as is commonly known. In one embodiment, the compressed gas cylinder 27 is a 25 g cylinder. Compressed gas leaves the black rock regulator 140 through a 10/32" hose port 12b and flows through a hose junction 22, by means of a ⅛" pressure hose 54, until reaching the 10/32" hose port 12 affixed to solenoid 55. From the hose port 12, the compressed gas enters the solenoid 55. The compressed gas unit 1 also has an outlet air port 25, which is connected to the solenoid 55 through intermediate a 10/32" hose port 12a for transporting compressed gas, namely $CO_2$, from the solenoid 55 in the compressed gas unit 1 to a foam generating catheter 2, whenever solenoid 55 is opened. Outlet gas may be monitored with a pressure gauge 52 connected to the hose junction 22 through a conduit 45 having threads 46. The threaded end of the conduit 45 interengages a nut 48 carried by the hose junction 22.

In certain embodiments a second compressed gas cylinder 28, featuring a 12 g or 16 g compressed gas cylinder, may be used in addition to or in lieu of the gas cylinder 27. In still other embodiments a larger compressed gas cylinder and expansion chamber may be substituted for the gas cartridges previously described in accordance with the invention. The size and number of compressed gas containers are not limitations of the invention.

Although a preferred compressed gas unit is disclosed above, it is appreciated other systems for the supply of compressed gas may be employed, for example, a system such as disclosed in U.S. patent application Ser. No. 14/957,657, filed Sep. 26, 2014, entitled "DELIVERY SYSTEM FOR THE EFFECTIVE, RELIABLE AND FOOLPROOF DELIVERY OF CONTROLLED AMOUNTS OF A MEDICAL FLUID," which is incorporated herein by reference.

Figure 2:
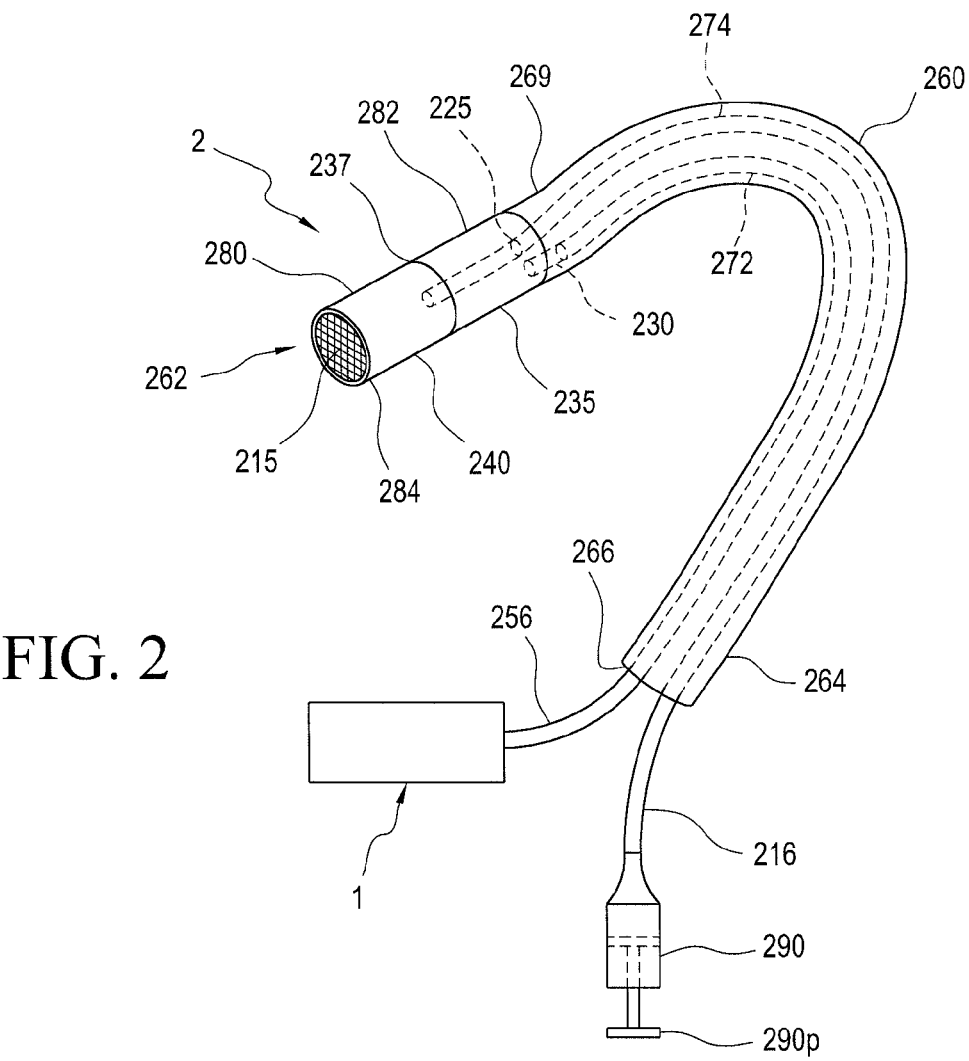
FIG. 2 is a perspective view of the foam generating catheter and a syringe containing a sclerosing agent.

With reference to FIG. 2, a $CO_2$ enriched foam generating catheter 2 features a dual lumen catheter 260 connecting a foam generating tip assembly 280 to compressed gas from the compressed gas unit 1 and a medical solution from a syringe 290. The foam generating catheter 2 includes a first end (or distal end) 262 having the foam generating tip assembly 280 and a second end (or proximal end) 264 to which the compressed gas unit 1 and the medical solution are fluidly connected for the passage of compressed gas and medical solution. As will be appreciated based upon the following disclosure, a dual lumen catheter 260 is connected to the foam generating tip assembly by securing a gas hose inlet 230 and a foam solution delivery line 225 of the foam generating tip assembly 280 to a first lumen 272 and a second lumen 274 of the dual lumen catheter 260, respectively.

A micro hose 256 connects the compressed gas unit 1 to the first lumen 272 of the dual lumen catheter 260 at a proximal first end 266 thereof for the transmission of the compressed gas from compressed gas unit 1 to the foam generating tip assembly 280. As such, compressed $CO_2$ leaving the compressed gas unit 1 via the outlet air port 25 enters the first lumen 272 of the dual lumen catheter 260 via micro hose 256. After passing through the first lumen 272 of the dual lumen catheter 260, the compressed gas passes through gas hose inlet 230 of the foam generating tip assembly 280 and enters the foam generating tip assembly 280 of the foam generating catheter 2. As will be explained below in greater detail, foam generated at the foam generating tip assembly 280 is directly applied to a vein requiring treatment with a sclerosing agent that has been integrated into the $CO_2$ enriched medical foam.

As to the connection of the medical solution to the foam generating catheter 2, the medical solution, which in accordance with a preferred embodiment of the present invention is a sclerosing agent, is delivered to the second lumen 274 of the dual lumen catheter 260 at the proximal first end 266 thereof, and ultimately to the foam generating tip assembly 280, via a container, in particular, a syringe 290, connected to the second lumen 274 of the dual lumen catheter 260 by a supply line 216. After passing through the second lumen 274 of the dual lumen catheter 260, the sclerosing agent from the syringe 290 travels into the solution delivery line 225 of the foam generating tip assembly 280 where it is combined with compressed gas from the compressed gas unit 1.

Figure 3:
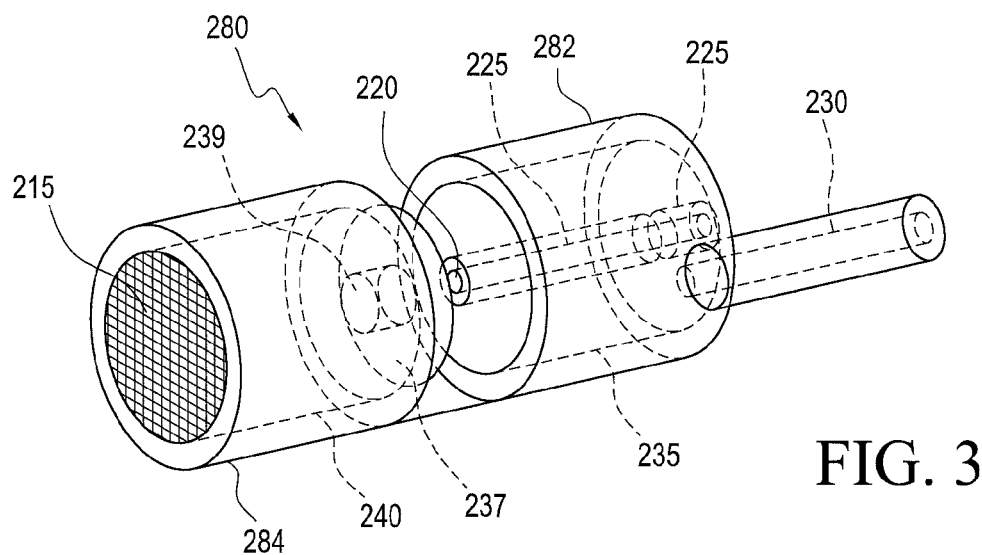
FIG. 3 is a close-up exploded view of the foam generating tip assembly shown in FIG. 2.

As shown in FIGS. 2 and 3, and as briefly discussed above, the foam generating tip assembly 280 includes a proximal first end 282 and a distal second end 284. The foam generating tip assembly 280 includes an upper chamber 240 at the distal second end 284 of the foam generating tip assembly 280 and a lower chamber 235 at the proximal first end 282 of the foam generating tip assembly 280, wherein a distal second end 269 of the dual lumen catheter 260 is fluidly coupled to the lower chamber 235 at the proximal first end 282 of the foam generating tip assembly 280. The upper chamber 240 and the lower chamber 235 are separated by a wall 237 having an aperture 239 formed therein allowing for the passage of compressed gas released in the lower chamber 235 to pass into the upper chamber 240.

The foam solution delivery line 225 passes through the lower chamber 235 and has an outlet 220 for delivering the medical solution into the upper chamber 240. As discussed above, the medical solution is a sclerosing agent delivered to the foam solution delivery line 225 via the syringe 290 and the dual lumen catheter 260. More particularly, the sclerosing agent from the syringe 290 travels through the second lumen 274 of the dual lumen catheter 260 and into the solution delivery line 225 when compressed gas enters the foam generating tip assembly 280 through the inlet 230 after being actuated and released from the compressed gas unit 1. The compressed gas entering the foam generating tip assembly 280 imparts negative pressure on the sclerosing agent in the syringe 290 and draws the sclerosing agent from the syringe 290 through the supply line 216, through the second lumen 274 of the dual lumen catheter 260, and into the solution delivery line 225 due to the Venturi effect. The syringe plunger 290p is used to regulate or stop flow of sclerosing agent from the syringe 290. Compressed gas traveling from the lower chamber 235 of the foam generating tip assembly 280 to the upper chamber 240 of the foam generating tip assembly via aperture 239 in the wall 237 creates negative pressure inside the foam generating tip assembly 280, such that medical foam solution exiting the outlet 220 of the solution delivery line 225 mixes with compressed $CO_2$ and forms $CO_2$ enriched medical foam (integrated with the sclerosing agent) that forms on the porous membrane 215. The force of the compressed gas traveling through the foam generating tip assembly 280 and exiting through the porous membrane 215 lifts medical foam/foams outward from the porous membrane 215 and projects the foam from the distal second end 284 of the foam generating tip assembly 280.

It is appreciated various tip assemblies and foam generating structures may be employed in accordance with the present invention. In accordance with a first alternate embodiment as shown with reference to FIGS. 4A-4C, the foam generating tip assembly 380 employs a Venturi arrangement with a mixing chamber 324. The foam generating tip assembly 380 has a proximal first end 380a and a distal second end 380b. The foam generating tip assembly 380 includes a hollow cylindrical elongated body 310 having a proximal first end 312, which coincides with the proximal first end 380a of the foam generating tip assembly 380, and a distal second end 314. The proximal first end 380a of the foam generating tip assembly 380 includes a multi-channel arrangement 381 including first and second inputs 316, 318 for attachment to the dual lumen catheter 360. The first and second inputs 316, 318 respectively lead to a first channel 320 and a second channel 322 of the multi-channel arrangement 381 of the foam generating tip assembly 380. The first and second channels 320, 322 lead to, and are in fluid communication with, a mixing chamber 324 (which also forms part of the multi-channel arrangement 381) located in the central portion 326 of the foam generating tip assembly 380, that is, between the proximal first end 380a and the distal second end 380b. Located at the distal second end 380b of the foam generating tip assembly 380, and secured to the distal second end 414 of the elongated body 310, is a tip member 328 composed of a sintered material having a porous structure allowing for the passage of the pressurized $CO_2$ and sclerosing agent.

The first channel 320 and the second channel 322 are interconnected in a manner creating a Venturi effect causing the pressurized $CO_2$ to effectively pull the sclerosing agent through the second channel 322 and into the mixing chamber 324. This is achieved by providing with the first channel 320 with a reduced diameter as it extends from the proximal first end 312 of the elongated body 310 (that is, the first end 320a of the first channel 320) to the central portion 326 of the foam generating tip assembly 380 (that is, the second end 320b of the first channel 320). In accordance with a preferred embodiment, the diameter of the first channel 320 decreases from a diameter of 0.038 inches adjacent the proximal first end 312 of the elongated body 310 to a diameter of 0.017 inches adjacent the mixing chamber 324.

As mentioned above, the second channel 322 is in fluid communication with the first channel 320. This is achieved by the provisional of a transverse channel 330 connecting the second end 320b of the first channel 320 with the second end 322b of the second channel 322. In particular, the second channel 322 includes a first end 322a adjacent the proximal first end 312 of the elongated body 310 and a second end 322b adjacent the mixing chamber 324 (although not directly in fluid communication with the mixing chamber 324) and the transverse channel 330. In accordance with a preferred embodiment, the diameter of the second channel 322 is 0.031 inches and remains consistent as it extends from the first end 322a thereof to the second end 322b thereof.

The first lumen 372 of a dual lumen catheter 360 supplies the pressurized $CO_2$ and the second lumen 374 supplies the sclerosing agent. As such, the first lumen 372 is connected to, and in fluid communication with, the first channel 320 of the foam generating tip assembly 380 and the second lumen 374 is connected to, and in fluid communication with, the second channel 322 of the foam generating tip assembly 380. In practice, and as described above in conjunction with the prior embodiment, the sclerosing agent from the syringe 290 travels through the second lumen 374 of the dual lumen catheter 360 and into the second channel 322 when pressurized $CO_2$ gas enters the first channel 320 and passes the transverse channel 330 into the mixing chamber 324 after being actuated and released from the compressed gas unit 1. The pressurized $CO_2$ entering the foam generating tip assembly 380 imparts negative pressure on the sclerosing agent in the syringe 290 and draws the sclerosing agent from the syringe 290 through the second channel 322, through the second lumen 374 of the dual lumen catheter 360, and into the mixing chamber 324 due to the Venturi effect. The syringe plunger 290p is used to regulate or stop flow of sclerosing agent from the syringe 290.

The pressurized $CO_2$ and sclerosing agent mixing in the mixing chamber 324 are then forced through the sintered material tip 328 where $CO_2$ enriched medical foam (integrated with the sclerosing agent) forms on the exterior surface 328a of the sintered material tip 328. In particular, the force of the pressurized $CO_2$ traveling through the foam generating tip assembly 380 and exiting through the sintered material tip 328 lifts the medical foam/foams outward from the exterior surface 328a of the sintered material tip 328 and projects the foam from the second end 380b of the foam generating tip assembly 380.

In accordance with a second embodiment as shown with reference to FIGS. 5A-5D, a foam generating tip assembly 480 employs a sintered material tip 428 in conjunction with a multi-channel arrangement 481 where the pressurized $CO_2$ and sclerosing agent are mixed and forced through the sintered material tip 428. The foam generating tip assembly 480 includes a proximal first end 480a and a distal second end 480b. The foam generating tip assembly 480 includes a hollow cylindrical elongated body 410 having a proximal first end 412, which coincides with the proximal first end 480a of the foam generating tip assembly 480, and a distal second end 414. The foam generating tip assembly 480 is adapted for use with a dual lumen catheter 460, in particular a dual lumen catheter having concentric lumens, wherein the outer first lumen 472 is annular shaped for the passage of pressurized $CO_2$ (and has an outer diameter of 0.092 inches at the outer wall thereof and an inner diameter of 0.042 inches at the inner wall thereof) and the inner second lumen 474 is circular shaped for the passage of the sclerosing agent (and has a diameter of 0.030 inches). The inner second lumen 474 is supported within the outer first lumen 472 by first and second radially extending rib members 473a, 473b (each having a thickness of 0.006 inches) that extend from the outer surface of the second lumen 474 to the inner surface of the outer first lumen 472. In this way the outer first lumen 472 is divided into first and second semicircular passageways 475a, 475b.

The proximal first end 480a of the foam generating tip assembly 480, in particular, the proximal first end 412 of the elongated body 410 is formed with two projections 432, 434 shaped and dimensioned for engagement within the outer first lumen 472 of the catheter 460 in a manner blocking a substantial portion of the outer first lumen 472. The two projections 432, 434 are arcuate members shaped and dimensioned to respectively block substantial portions of the first and second semicircular passageways 475a, 475b while creating four small passageways 436, each of approximately 0.031 inches (along the Y-axis as shown in FIG. 5D) by 0.050 inches (along the X-axis as shown in FIG. 5D) for the passage of pressurized $CO_2$ therethrough. The four small passageways 436 are defined by spaces existing between the edges of the arcuate members 432, 434 and the first and second radially extending rib members 473a, 473b.

The remainder of the foam generating tip assembly 480 includes a central mixing chamber 424 that is in fluid communication with the second lumen 474 and the four small passageways 436 feeding pressurized $CO_2$ from the first lumen 472. Secured to, and closing off, the second end 414 of the elongated body 410 is a sintered material tip 428, which is thereby positioned at the distal second end 480b of the foam generating tip assembly 480. Attachment of the sintered material tip 428 to the elongated body 410 is achieved by providing the sintered material tip 428 with a projection 438 that seats within the opening at the second end 414 of the elongated body 410.

The first lumen 472 and the second lumen 474 are interconnected in a manner causing the pressurized $CO_2$ to effectively pull the sclerosing agent through the second lumen 474 and into the mixing chamber 424. In practice, the sclerosing agent from the syringe 290 travels through the second lumen 474 of the dual lumen catheter 460 and into the mixing chamber 424 when compressed gas passes through the four small passageways 436 and enters the mixing chamber 424 after being actuated and released from compressed gas unit 1. The pressurized $CO_2$ entering the mixing chamber 424 imparts negative pressure on the sclerosing agent in syringe 290 and draws the sclerosing agent from the syringe 290 through the second lumen 474 and into the mixing chamber 424. The syringe plunger 290p is used to regulate or stop flow of sclerosing agent from the syringe 290.

The pressurized $CO_2$ and sclerosing agent mixing in the mixing chamber 424 are then forced through the sintered material tip 428 where $CO_2$ enriched medical foam (integrated with the sclerosing agent) forms on the exterior surface 428a of the sintered material tip 428. In particular, the force of the pressurized $CO_2$ traveling through the foam generating tip assembly 480 and exiting through the sintered material tip 428 lifts the medical foam/foams outward from the exterior surface 428a of the sintered material tip 428 and projects the foam from the second end 480b of the foam generating tip assembly 480.

Figure 6:
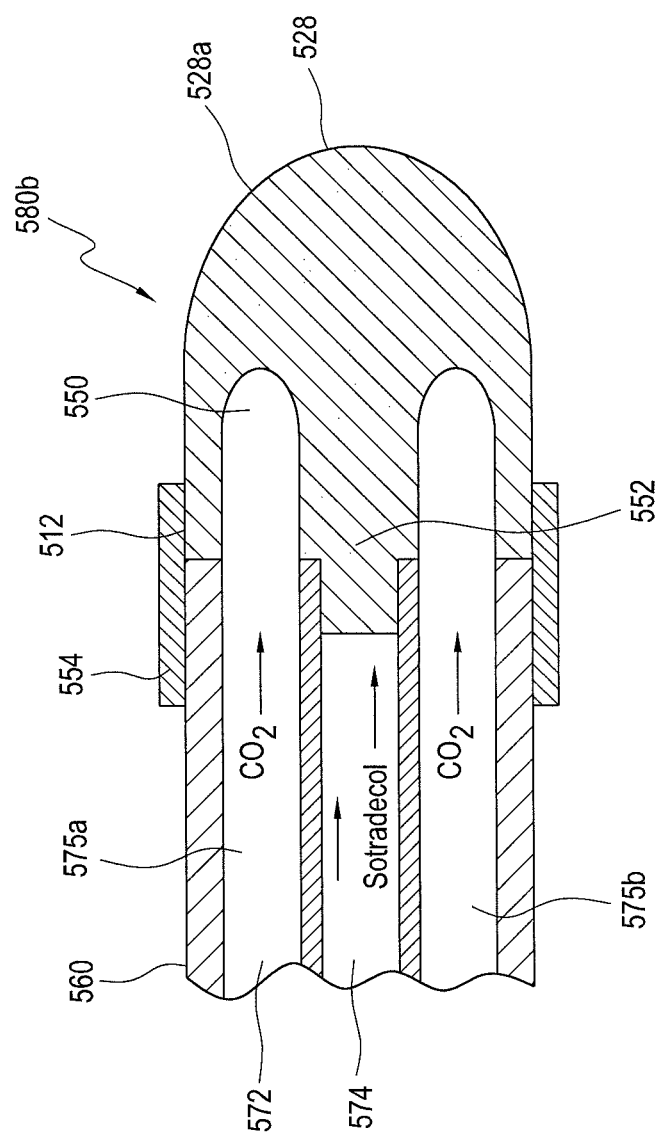
FIG. 6 is a cross-sectional view of a foam generating tip assembly in accordance with an alternate third embodiment.
Figure 8E:
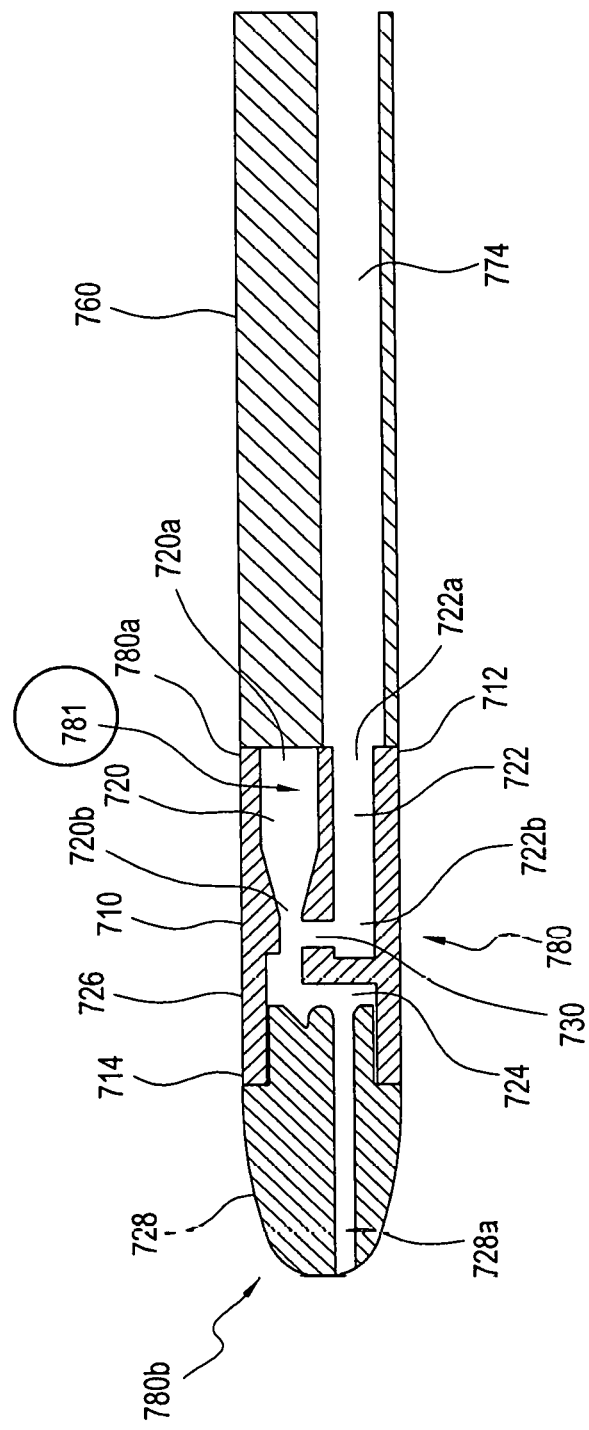

In accordance with a third embodiment as shown with reference to FIG. 6, a foam generating tip assembly 580 is composed solely of a porous sintered material tip 528 shaped and dimensioned for attachment to the end of a dual lumen catheter 560, in particular, a dual lumen catheter 560 having concentric lumens, wherein the outer first lumen 572 is annular shaped for the passage of pressurized $CO_2$ (and has an outer diameter of 0.092 inches at the outer wall thereof and an inner diameter of 0.042 inches at the inner wall thereof) and the inner second lumen 574 is circular shaped for the passage of the sclerosing agent (and has a diameter of 0.030 inches). The inner second lumen 574 is supported within the outer first lumen 572 by first and second radially extending rib members (as shown in FIGS. 5C and 5D) that extend from the outer surface of the second lumen 574 to the inner surface of the outer first lumen 572. In this way the outer first lumen 572 is divided into first and second semicircular passageways 575a, 575b.

The proximal first end 512 of the sintered material tip 528 is formed with a circular recess 550 shaped and dimensioned to correspond with the outlet of the first lumen 572 at the distal end of the dual lumen catheter 560. A longitudinally extending projection 552 extends from the center of the proximal first end 512 and is shaped and dimensioned for frictional placement within the central second lumen 574 so as to close off (with the exception of the porous nature of the sintered material tip) the second lumen 574. The attachment of the sintered material tip 528 at the distal end of the dual lumen catheter 560 is achieved by the provision of a shrink wrap member 554 at the junction of the dual lumen catheter 560 with the sintered material tip 528.

The first lumen 572 and the second lumen 574 are interconnected via the sintered material tip 528 in a manner causing the pressurized $CO_2$ to effectively pull the sclerosing agent through the second lumen 574 and into the sintered material tip 528 where they mix and are ultimately forced through the sintered material tip 528. In practice, the sclerosing agent from syringe 290 travels through the second lumen 574 of the dual lumen catheter 560 and into the sintered material tip 528 when pressurized $CO_2$ passes through the first lumen 572 and into the sintered material tip 528. The pressurized $CO_2$ entering the sintered material tip 528 imparts negative pressure on the sclerosing agent in syringe 290 and draws the sclerosing agent from the syringe 290 through the second lumen 574 and into the sintered material tip 528. The syringe plunger 290p is used to regulate or stop flow of sclerosing agent from the syringe 290.

The pressurized $CO_2$ and sclerosing agent mixing in the sintered material tip 528 are then forced through the sintered material tip 528 where $CO_2$ enriched medical foam (integrated with the sclerosing agent) forms on the exterior surface 528a of the sintered material tip 528. In particular, the force of the pressurized $CO_2$ traveling through the foam generating tip assembly 580 and exiting through the sintered material tip 528 lifts the medical foam/foams outward from the exterior surface 528a of the sintered material tip 528 and projects the foam from the second end 580b of the foam generating tip assembly 580.

In accordance with a fourth embodiment as shown with reference to FIGS. 7A and 7B, a foam generating tip 680 employs a porous screen tip 628 in conjunction with a multi-channel arrangement 681 where the pressurized $CO_2$ and sclerosing agent are mixed and forced through the screen tip 628. The foam generating tip assembly 680 includes a proximal first end 680a and a distal second end 680b. The foam generating tip assembly 680 includes a cylindrical hollow elongated body 610 having a proximal first end 612, which coincides with the proximal first end

680a of the foam generating tip assembly 680, and a distal second end 614, which coincides with the distal second end 680b of the foam generating tip assembly 680. The foam generating tip assembly 680 is adapted for use with a dual lumen catheter 660, in particular a dual lumen catheter having concentric lumens, wherein the outer first lumen 672 is annular shaped for the passage of pressurized $CO_2$ (and has an outer diameter of 0.092 inches at the outer wall thereof and an inner diameter of 0.042 inches at the inner wall thereof) and the inner second lumen 674 is circular shaped for the passage of the sclerosing agent (and has a diameter of 0.030 inches). The inner second lumen 674 is supported within the outer first lumen 672 by first and second radially extending rib members (as shown in FIGS. 5C and 5D) that extend from the outer surface of the second lumen 674 to the inner surface of the outer first lumen 672. In this way the outer first lumen 672 is divided into first and second semicircular passageways 675a, 675b.

The proximal first end 612 of the elongated body 610 at the proximal first end 680a of the foam generating tip assembly 680 includes an end wall 661 (created by adhesive injected to limit flow from the first lumen 672) with two projecting channels 662a, 662b (each with a diameter of 0.015 inches) shaped and dimensioned for engagement with the first and second semicircular passageways 675a, 675b. The end wall 660 of the proximal first end 612 of the elongated body 610 is also provided with a central aperture 664 shaped and dimensioned for alignment with the second lumen 674. The remainder of the proximal first end 612 of the elongated body 610 is closed off thus limiting and controlling the flow of materials into the central mixing chamber 624.

The remainder of the foam generating tip assembly 680 includes a central mixing chamber 624 that is in fluid communication with the second lumen 674 and the two projecting channels 662a, 662b feeding pressurized $CO_2$ from the first lumen 672. Secured to, and closing off, the second end 614 of the elongated body 610 is a screen tip 628, which is thereby positioned at the distal second end 680b of the foam generating tip assembly 680.

The first lumen 672 and the second lumen 674 are interconnected in a manner causing the pressurized $CO_2$ to effectively pull the sclerosing agent through the second lumen 674 and into the mixing chamber 624. In practice, the sclerosing agent from the syringe 290 travels through the second lumen 674 of the dual lumen catheter 660 and into the mixing chamber 624 when pressurized $CO_2$ passes through the first and second projecting channels 662a, 662b and enters the mixing chamber 624 after being actuated and released from the compressed gas unit 1. The pressurized $CO_2$ entering the mixing chamber 624 imparts negative pressure on the sclerosing agent in the syringe 290 and draws the sclerosing agent from the syringe 290 through second lumen 674 and into the mixing chamber 624. The syringe plunger 290p is used to regulate or stop flow of sclerosing agent from the syringe 290.

The pressurized $CO_2$ and sclerosing agent mixing in the mixing chamber 624 is then forced through the screen tip 628 where $CO_2$ enriched medical foam (integrated with the sclerosing agent) forms on the exterior surface 628a of the screen tip 628. In particular, the force of the pressurized $CO_2$ traveling through the screen tip 628 and exiting through the screen tip 628 lifts the medical foam/foams outward from the exterior surface 628a of the screen tip 628 and projects the foam from the second end 680b of the foam generating tip assembly 680.

In accordance with a fifth embodiment as shown with reference to FIGS. 8A-8E, a foam generating tip assembly 780 employs a tip 728 in conjunction with a multi-channel arrangement 781 where the pressurized $CO_2$ and sclerosing agent are mixed and forced through the tip 728. The foam generating tip assembly 780 includes proximal first end 780a and a distal second end 780b. The foam generating tip assembly 780 includes a hollow cylindrical elongated body 710 having a proximal first end 712, which coincides with the proximal first end 780a of the foam generating tip assembly 780, and a distal second end 714. The foam generating tip assembly 780 is adapted for use with a multi-lumen catheter 760, in particular a triple lumen catheter having parallel lumens, wherein the first and second lumens 772, 773 are circular shaped (each with a diameter of 0.039 inches) and are dimensioned for the passage of pressurized $CO_2$ and the third lumen 774 is semi-circular shaped (with a radius of 0.047 inches) and is dimensioned for the passage of the sclerosing agent.

The proximal first end 712 of the elongated body 710 at the proximal first end 780a of the foam generating tip assembly 780 includes first, second and third inputs 716, 717, 718 for attachment to the multi-lumen catheter 760. The first and second inputs 716, 717 lead to a first channel 720 and the third input 718 to a second channel 722. As such, the proximal first end 712 of the elongated body 710 at the proximal first end 780a of the foam generating tip assembly 780 is formed with two circular tubular projections 732, 734, defining the first and second inputs 716, 717. The circular tubular projections 732, 734 (each with an inner diameter of 0.027 inches and an outer diameter of 0.039 inches) are shaped and dimensioned for engagement within the first and second lumens 772, 773 of the catheter 760 in a manner allowing for the flow of fluid from the first and second lumens 772, 773 and into the foam generating tip assembly 780. The two circular tubular projections 732, 734 are shaped and dimensioned to fit within the first and second lumens 772, 773 while maintaining passageways for the passage of pressurized $CO_2$ therethrough.

The first and second channels 720, 722 lead to, and are in fluid communication with, a mixing chamber 724 located in the central portion 726 of the foam generating tip assembly 780, that is, between the proximal first end 712 and the distal second end 714 of the elongated body. Secured to the distal second end 714 of the elongated body 710, and positioned at the distal second end 780b of the foaming generating tip assembly, is a tip 728 having three passageways 728a, 728b, 728c extending from the mixing chamber 724 to the exterior at the distal end of the foam generating tip assembly 780.

The first channel 720 and the second channel 722 are interconnected in a manner creating a Venturi effect causing the pressurized $CO_2$ to effectively pull the sclerosing agent through the second channel 722 and into the mixing chamber 724. This is achieved by providing the first channel 720 with a reduced diameter (decreasing from 0.038 inches to 0.017 inches) as it extends from the proximal first end 712 of the elongated body 710 (that is, the first end 720a of the first channel 720) to the central portion 726 of the foam generating tip assembly 780 (that is, the second end 720b of the first channel 720). In accordance with a preferred embodiment, the diameter of the first channel 720 decreases from a diameter of 0.038 inches adjacent the proximal first end 712 of the elongated body 710 to a diameter of 0.017 inches adjacent the mixing chamber 724.

As mentioned above, the second channel 722 is in fluid communication with the first channel 720. This is achieved by the provisional of a transverse channel 730 connecting the second end 720b of the first channel 720 with the second end 722b of the second channel 722. In particular, the second channel 722 includes a first end 722a adjacent the proximal first end 712 of the elongated body 710 and a second end 722b adjacent the mixing chamber 724 (although not directly in fluid communication with the mixing chamber 724) and the transverse channel 730. In accordance with a preferred embodiment, the diameter of the second channel 722 is 0.047 inches and remains consistent as it extends from the first end 722a thereof to the second end 722b thereof.

The first and second lumens 772, 773 supply the pressurized $CO_2$ and the third lumen 774 supplies the sclerosing agent. As such, the first and second lumens 772, 773 are connected to, and in fluid communication, with the first channel 720 of the foam generating tip assembly 780 and the third lumen 774 is connected to, and in fluid communication, with the second channel 722 of the foam generating tip assembly 780. In practice, the sclerosing agent from syringe 290 travels through third lumen 774 of multi-lumen lumen catheter 760 and into the second channel 722 when pressurized $CO_2$ gas enters the first channel 720 and passes the transverse channel 730 (having a size of 0.020 inches) into the mixing chamber 724 after being actuated and released from compressed gas unit 1. The pressurized $CO_2$ entering the foam generating tip assembly 780 imparts negative pressure on the sclerosing agent in syringe 290 and draws the sclerosing agent from the syringe 290 through second channel 722, through the third lumen 774 of the dual lumen catheter 760, and into the mixing chamber 724 due to the Venturi effect. The syringe plunger 290p is used to regulate or stop flow of sclerosing agent from the syringe 290.

The pressurized $CO_2$ and sclerosing agent mixing in the mixing chamber 724 are then forced through the passageways 728a-c of the tip 728 where $CO_2$ enriched medical foam (integrated with the sclerosing agent) forms on the exterior surface 728e of the tip 728. In particular, the force of the pressurized $CO_2$ traveling through foam generating tip assembly 780 and exiting through the tip 728 lifts the medical foam/foams outward from the exterior surface 728e of the tip 728 and projects the foam from the second end 780b of the foam generating tip assembly 780.

In accordance with the various embodiments described above, the $CO_2$ enriched medical foam then exiting the foam generating tip assembly is directed to a vessel requiring treatment. In accordance with a preferred embodiment, the method for vein treatment in accordance with the present invention is achieved in the following manner. The first end of the foam generating catheter, that is, foam generating tip assembly is introduced into a diseased/varicosed vein requiring treatment such that the first end of foam generating tip assembly is positioned beyond the section of vein requiring treatment. The second end of foam generating catheter is coupled to the compressed gas unit and the syringe. At this point, compressed gas unit is actuated to supply compressed gas, preferably, $CO_2$, to the foam dispensing catheter and $CO_2$ enriched medical foam is produced at foam generating tip assembly of foam dispensing catheter. The $CO_2$ enriched medical foam drips from the first end of foam generating tip assembly into the section of vein requiring treatment. As the catheter is withdrawn from the vein, $CO_2$ enriched medical foam is dribbled into the vein at various segments causing the vein to go into spasm resulting in eventual destruction of the diseased vein.

In accordance with yet another embodiment, the concepts underlying the present invention may be applied in the provision of a foam generating needle. Such a foam generating needle would be useful in accessing vessel locations that are inaccessible by the catheter described above. The needle embodiment may also be useful in accessing locations that are limited in length and might not require the use of the foam generating catheter described above.

Figure 11A:
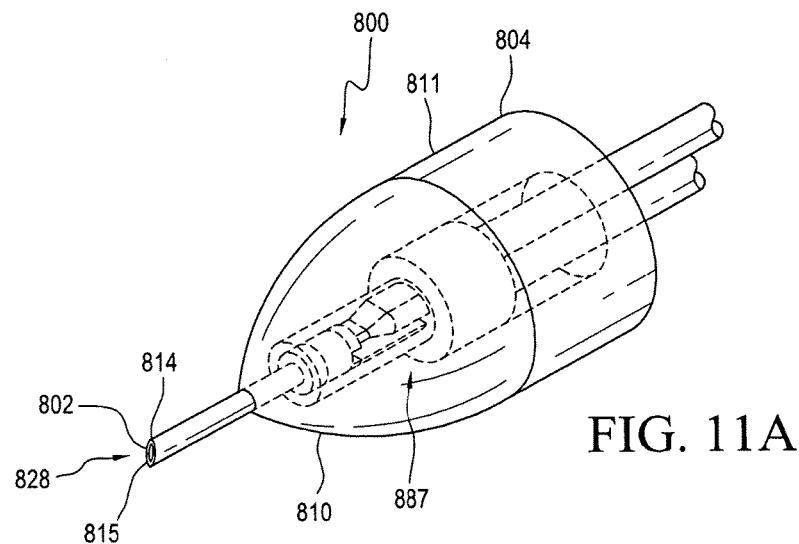
FIGS. 11A and 11B respectively show a perspective view and a cross-sectional view of a foam generating needle in accordance with the present invention.
Figure 11B:
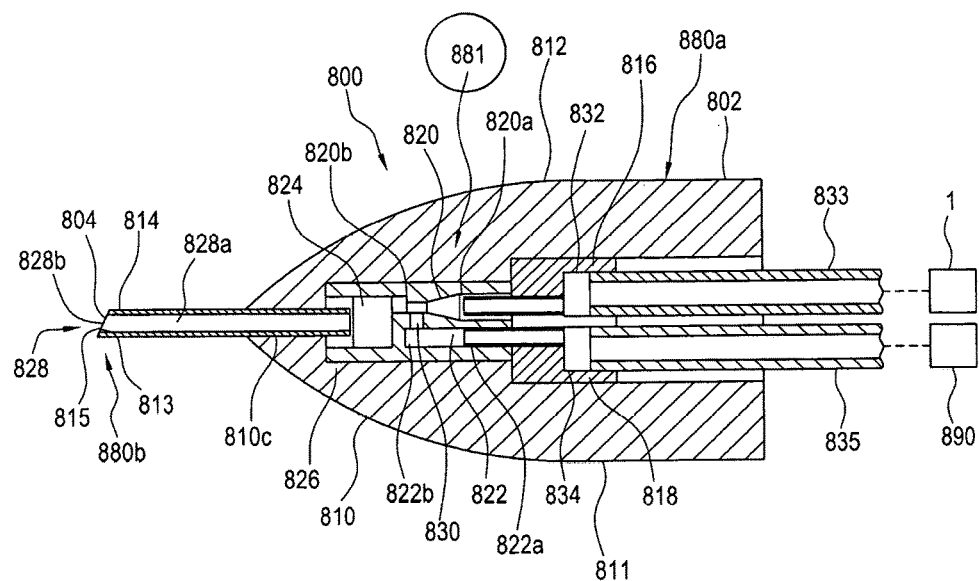

In accordance with such a foam generating needle embodiment, as shown with reference to FIGS. 11A, 11B and 11C, the foam generating needle 800 has a proximal first end 802, and a distal second end 804. In contrast to the prior embodiments, the foam generating needle 800 combines the compressed gas and the medical solution at the proximal first end 802 of the foam generating needle 800 and creates foam by the inclusion of a porous membrane 815 at the distal second end 804 of the foam generating needle 800. With this in mind, the foam generating needle 800 includes a hollow and substantially rigid elongated needle body 810. The needle body 810 includes a needle hub 811 at the proximal first end 812, which coincides with the proximal first end 802 of the foam generating needle 800, thereof and a sharp beveled edge 813 at the distal second end 814, which coincides with the distal second end 804 of the foam generating needle 800, thereof. With this in mind, and as will be appreciated based upon the following disclosure, the compressed gas source (that is, the compressed gas unit 1) and the medical solution source (that is, the syringe 290) are coupled to respective first and second inputs 816, 818 found within the needle hub 811 at the proximal end 804 of the foam generating needle 800.

As with the foam generating catheters discussed above, the foam generating needle 800 employs a tip 828 with a porous membrane 815 in conjunction with a multi-channel arrangement 881 where the pressurized $CO_2$ and sclerosing agent are mixed and forced through the tip 828 under the force generated by the Venturi system implemented in accordance with the present invention. The foam generating tip assembly 880 in accordance with the foam generating needle 800 of the present embodiment includes the tip 828 and the multi-channel arrangement 881 that are separated along the length of the needle body 810. However, the foam generating tip assembly 880 is integrally formed with the needle body 810 and the foam generating tip assembly 880 is considered to include a proximal first end 880a (that coincides with the proximal first end 802 of the foam generating needle 800) and a distal second end 880b (that coincides with the distal second end 804 of the foam generating needle 800 and is found in the needle hub 811). As such, the foam generating tip assembly 880 includes the hollow cylindrical elongated body 810 of the foam generating needle 800 as well as the internal flow controlling components discussed herein. As for the needle body 810, and with the exception of the multi-channel arrangement 881 found in the needle hub 811 at the proximal first end 802 of the foam generating needle 800, it is of a single lumen construction and includes a single lumen cannula 810c along that portion distal to the multi-channel arrangement 881 and the hub 811.

The multi-channel arrangement 881 found in the needle hub 811 at the proximal first end 880a of the foam generating tip assembly 880 includes first and second inputs 816, 818 for attachment to the compressed gas source (that is, the compressed gas unit 1) and the medical solution (that is, the syringe 290). The first input 816 leads to a first channel 820 and the second input 818 leads to a second channel 822. The proximal first end 880a of the foam generating tip assembly 880, and therefore the proximal first end 812 of the needle body 810, is formed with two circular tubular female coupling recesses 832, 834, defining the first and second inputs 816, 818. The coupling recesses 832, 834 are shaped and dimensioned for fluid coupling with the compressed gas source (that is, the compressed gas unit 1) and the medical solution (that is, the syringe 290), for example, via flexible cannulas 833, 835, in a manner allowing for the flow of fluid from the compressed gas unit 1 and the syringe 290), and into the needle body 810.

The first channel 820 leads to, and is in fluid communication with, a mixing chamber 824 located in the central portion 826 of the foam generating tip assembly 880, that is, between the proximal first end 880a and the distal second end 880b. Located at the distal second end 880b is a tip member 828 having a passageway 828a extending from the mixing chamber 824 to the exterior at the distal end 880b of the foam generating tip assembly 880.

The first channel 820 and the second channel 822 are interconnected in a manner creating a Venturi effect causing the pressurized $CO_2$ to effectively pull the sclerosing agent through the second channel 822 and into the mixing chamber 824. This is achieved by providing the first channel 820 with a reduced diameter as it extends from the proximal first end 812 of the needle body 810 (that is, the first end 820a of the first channel 820) to the central portion 826 of the elongated body 810 (that is, the second end 820b of the first channel 820).

As mentioned above, the second channel 822 is in fluid communication with the first channel 820. This is achieved by the provisional of a transverse channel 830 connecting the second end 820b of the first channel 820 with the second end 822b of the second channel 822. In particular, the second channel 822 includes a first end 822a adjacent the proximal first end 812 of the elongated body 810 and a second end 822b adjacent the mixing chamber 824 (although not directly in fluid communication with the mixing chamber 824) and the transverse channel 830.

The compressed gas source supplies the pressurized $CO_2$ and the medical solution source supplies the sclerosing agent. As such, the compressed gas source is connected to, and in fluid communication with, the first channel 820 of the foam generating tip assembly 880 and the medical solution source is connected to, and in fluid communication with, the second channel 822 of the foam generating tip assembly 880. In practice, a syringe 290 containing sclerosing agent is secured to the second input 818 at the proximal first end 802 of the foam generating needle 800 via a flexible cannula 833 and the $CO_2$ from the compressed gas unit 1 is secured to the first input 816 at the proximal first end 802 of the foam generating needle 800 via a flexible cannula 835. The sclerosing agent from the syringe 290 travels through second input 818 and into the second channel 822 when pressurized $CO_2$ gas enters the first channel 820 and passes the transverse channel 830 into the mixing chamber 824 after being actuated and released from compressed gas unit 1. The pressurized $CO_2$ entering the foam generating tip assembly 880 imparts negative pressure on the sclerosing agent in syringe 290 and draws the sclerosing agent from the syringe 290 through second channel 822, through second input 818 of the foam generating needle 800, and into the mixing chamber 824 due to the Venturi effect. The syringe plunger 290p is used to regulate or stop flow of sclerosing agent from syringe 290.

The pressurized $CO_2$ and sclerosing agent mixing in the mixing chamber 824 are then forced through the remainder of the needle body 810, in particular, the single lumen portion thereof, and through the porous membrane 815 at the tip 828 where the $CO_2$ enriched medical foam (integrated with the sclerosing agent) forms at the end 828e of the tip 828. In particular, the force of the pressurized $CO_2$ traveling through the porous membrane 815 of the foam generating tip assembly 880 and exiting through the tip 828 lifts the medical foam/foams outward from the end 828e of the tip 828 and projects the foam from the distal second end 880b of foam generating tip assembly 880.

It will be appreciated the fluid mechanics of the foam generating needle embodiment are similar to those of the embodiment discussed with reference to FIGS. 8A-8D, and the dimensions would therefore be similar.

As the needle embodiment shows, the concepts underlying the present invention may be implemented using a needle, that is, a rigid cannula, or a catheter, that is, a flexible cannula. Accordingly, the term foam generating cannula should be considered to encompass both those embodiments implemented using a catheter and those embodiments using a needle.

It is appreciated this procedure can be performed under ultrasound guidance or radiograph in order for the physician to control the amount of liquid to mix with the $CO_2$ gas to form the foam. The medical solution may be varied depending on the medical need for the individual vessel/patient.

Further to the general method for vein treatment as discussed above, it is contemplated the present foam generating catheter may be utilized in the treatment of the great saphenous vein. As those skilled in the art will appreciate, the great saphenous vein is a large, subcutaneous, superficial vein of the leg. It is the longest vein of the body running along the length of the leg. In particular, the great saphenous vein originates from where the dorsal vein of the first digit (that is, the large toe) merges with the dorsal venous arch of the foot. The great saphenous vein extends along the inner portion of the leg until it reaches the common femoral vein in the region of the femoral triangle at the sapheno-femoral junction. Given its size, the great saphenous vein is highly related to vascular issues relating to vein ablation. With this in mind, the present foam generating catheter is utilized so as to apply sclerosing foam within the great saphenous vein in an effective manner for the treatment and ablation thereof.

With this in mind, the foam generating tip assembly is introduced into the great saphenous vein. As discussed above, with the first end of the foam generating tip assembly positioned beyond the section of the great saphenous vein requiring treatment, the second end of the foam generating catheter is coupled to the compressed gas unit and the syringe. At this point, the compressed gas unit is actuated to supply compressed gas, preferably, $CO_2$, to foam dispensing catheter and $CO_2$ enriched medical foam is produced at the foam generating tip of the foam dispensing catheter. The $CO_2$ enriched medical foam drips from the membrane at the first end of the foam generating tip assembly into the section of the great saphenous vein requiring treatment. As the $CO_2$ enriched medical foam is permitted to drip, the catheter is withdrawn from the vein and the $CO_2$ enriched medical foam is dribbled into the vein at various segments causing the vein to go into spasms resulting in eventual destruction of the diseased vein. More particularly, and considering a minimal incisional approach at the medial aspect of the knee at the area of the distal end of the great saphenous vein, the foam generating catheter is inserted upward toward the sapheno-femoral junction at the proximal end of the great saphenous vein, at the thigh area. Once the foam generating tip assembly is properly positioned, the foam is produced at the tip of the catheter, it is then deposited in the segments of the vessel of the great saphenous vein at the portion of the vein that will react to the foam and subsequently put the vein segment into spasm. Then, as the foam generating catheter is removed, more distal portions of the vein are caused to spasm and the foam generating catheter is withdrawn at the point of insertion at the knee area of the great saphenous vein. In accordance with such a procedure when employing the present foam generating catheter, sclerosing foam is used to contact the entire lumen of the great saphenous vein, rather than sclerosing liquid which often lays in the bottom of the lumen of the vessel and then only kills off that portion of the lumen usually resulting in recanalization of the vein and subsequently high recurrence of the problem.

In addition to the treatment of the great saphenous vein, the present foam generating catheter may be used in the treatment of various vascular ailments. Given that present foam generating catheter employs pure $CO_2$ the present foam generating catheter is useful in treating arterial ailments as well as treating vascular ailments. As those skilled in the art will appreciate, it is not acceptable to use oxygen for certain procedures within the arterial system given the susceptibility of air embolisms within the arterial system. When using room air or oxygen, the chance of anoxia to the brain, eschemia of the brain, air embolism and stroke are much more prevalent than when using $CO_2$, which very rarely ever causes that type of complication within the venous tree. Also when using room air or oxygen, you cannot use these substances/gases in the arterial tree of the human body. The potential treatments that may employ the present foam generating catheter include, but are not limited to the following, some of these ailments relate to the extremity venous varices (venous), varicocoel (venous), pelvic congestion syndrome (venous), symptomatic vascular malformation (arterial and venous), portal vein embolization (venous), organ/tumor ablation (arterial), BRTO (balloon-occluded retrograde transvenousobliteration) (venous), CARTO (above but with coils) (venous), arterial delivery for hepatic chemoembolization in renal failure patients (arterial), and TACE Procedure/mixing gas and solution or solutions and solutions not to create foam (arterial and venous).

Figure 9:
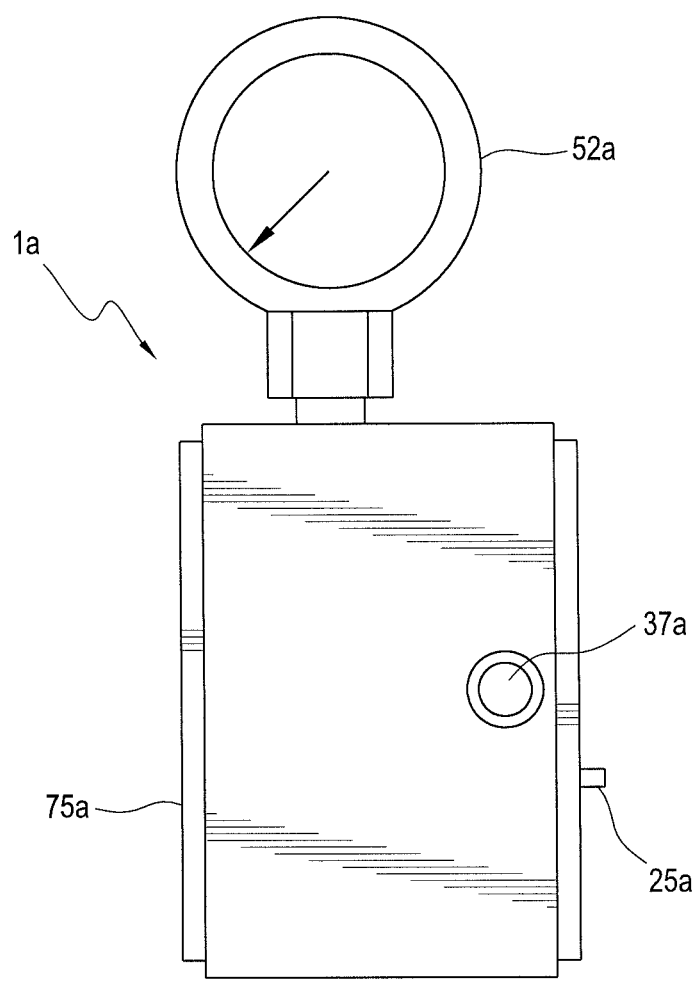
FIG. 9 is a schematic front view of an alternative compressed gas unit enclosed in a housing.
Figure 10:
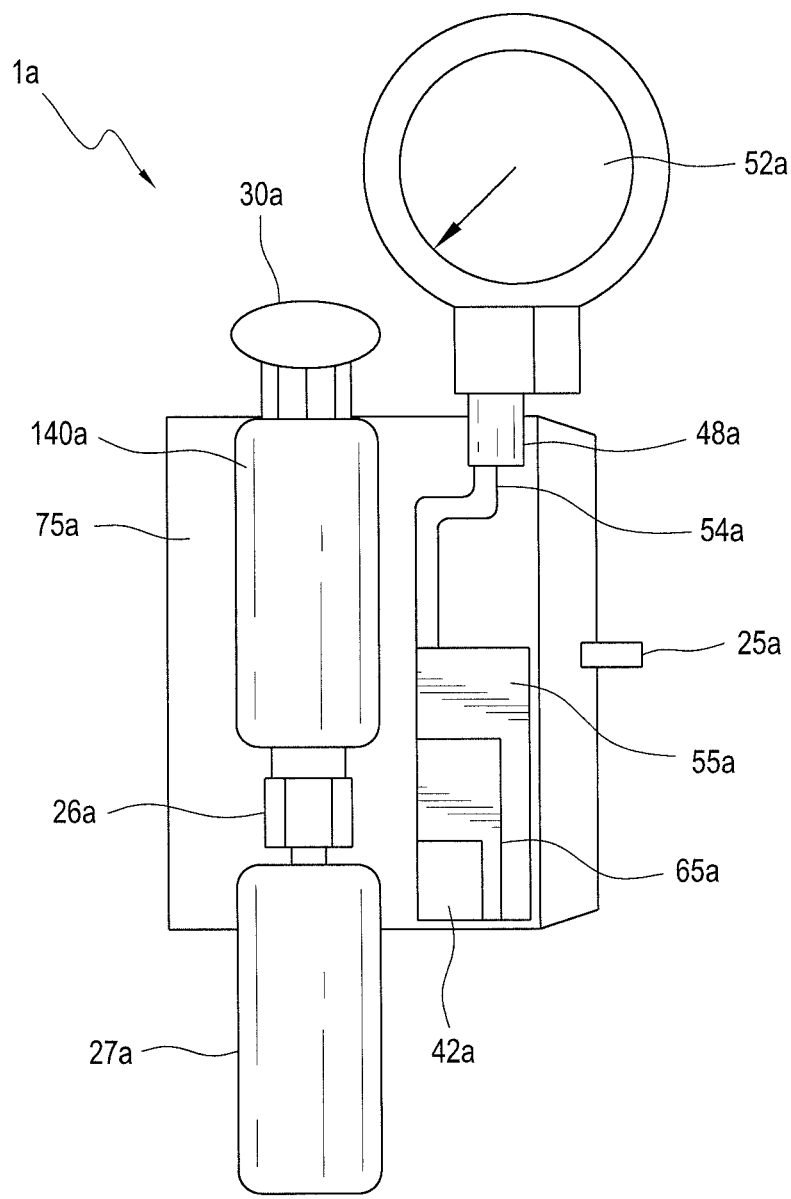
FIG. 10 depicts a schematic layout of the components of the compressed gas unit of FIG. 9.

FIGS. 9 and 10 depict an alternative embodiment of a compressed gas unit 1a wherein various components of the gas unit are enclosed in a housing 75. The components of unit 1a are designated by reference numerals that correspond to those of the previously described embodiment and further include "a" designations. In particular, a $CO_2$ cartridge 27a is connected by a puncture valve 26a to a regulator 140a. The regulator is controlled by an adjustment knob 30a. Regulator 140a is connected through a conduit 54a to both a pressure gauge 52a and a solenoid 55a. More particularly, gauge 52a is connected to a coupling 48a. Solenoid 55a is powered by a battery 65a, which is itself held in place within the housing by a holder 42a. A user accessible luer fitting 25a is communicably connected to solenoid 55a and extends exteriorly of housing 75a.

Unit 1a is activated to open solenoid 55a by engaging switch 37a. The compressed gas unit operates in a manner analogous to that previously described to provide compressed $CO_2$ from cartridge 27a through luer fitting 25a to an attached foam generating tip as depicted in FIGS. 2 and 3.

While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. A gas enriched foam generating apparatus for performing medical procedures, comprising:
    a foam generating tip assembly composed of a multi-channel arrangement at a proximal first end thereof and a tip at a distal second end thereof;
    a compressed gas unit fluidly connected to the multi-channel arrangement at a proximal first end of the foam generating tip assembly; and
    a medical solution fluidly connected to the multi-channel arrangement at a proximal first end of the foam generating tip assembly;
    wherein compressed gas, from the compressed gas unit, and the medical solution are combined within the foam generating tip assembly in a manner generating a gas enriched foam that is ultimately dispensed from the foam generating apparatus; and
    further including a dual lumen catheter including a first end and a second end to which the foam generating tip assembly is secured.

2. The foam generating apparatus according to claim 1, wherein the compressed gas unit is fluidly connected to a first lumen of the dual lumen catheter.

3. The foam generating apparatus according to claim 2, wherein the medical solution is fluidly connected to a second lumen of the dual lumen catheter.

4. The foam generating apparatus according to claim 3, wherein the multi-channel arrangement of the foam generating tip assembly employs a Venturi arrangement with a mixing chamber.

5. The foam generating apparatus according to claim 4, wherein the tip is composed of a sintered material having a porous structure allowing for the passage of the pressurized gas and the medical solution.

6. A medical method, comprising:
    treating arteries using the foam generating apparatus according to claim 2.

7. A medical method, comprising:
    treating veins using the foam generating apparatus according to claim 2.

8. The medical method according to claim 7, wherein the vein is the great saphenous vein.

9. The foam generating apparatus according to claim 1, wherein the compressed gas is pressurized $CO_2$.

10. A gas enriched foam generating apparatus for performing medical procedures, comprising:
    a foam generating tip assembly composed of a multi-channel arrangement at a proximal first end thereof and a tip at a distal second end thereof;
    a compressed gas unit fluidly connected to the multi-channel arrangement at a proximal first end of the foam generating tip assembly; and
    a medical solution fluidly connected to the multi-channel arrangement at a proximal first end of the foam generating tip assembly;
    wherein compressed gas, from the compressed gas unit, and the medical solution are combined within the foam generating tip assembly in a manner generating a gas enriched foam that is ultimately dispensed from the foam generating apparatus; and wherein the foam generating tip assembly includes a tip member composed of a sintered material having a porous structure allowing for the passage of the pressurized gas and the medical solution.

11. The foam generating apparatus according to claim 10, wherein the compressed gas is pressurized $CO_2$.

12. A medical method, comprising:
treating arteries using the foam generating apparatus according to claim 10.

13. A medical method, comprising:
treating veins using the foam generating apparatus according to claim 10.

14. The medical method according to claim 13, wherein the vein is the great saphenous vein.

15. A gas enriched foam generating apparatus for performing medical procedures, comprising:
a foam generating tip assembly composed of a multi-channel arrangement at a proximal first end thereof and a tip at a distal second end thereof;
a compressed gas unit fluidly connected to the multi-channel arrangement at a proximal first end of the foam generating tip assembly; and
a medical solution fluidly connected to the multi-channel arrangement at a proximal first end of the foam generating tip assembly;
wherein compressed gas, from the compressed gas unit, and the medical solution are combined within the foam generating tip assembly in a manner generating a gas enriched foam that is ultimately dispensed from the foam generating apparatus; and
wherein the medical solution is a sclerosing agent.

16. The foam generating apparatus according to claim 15, further including a further including a dual lumen catheter including a first end and a second end to which the foam generating tip assembly is secured.

17. The foam generating apparatus according to claim 16, wherein the compressed gas unit is fluidly connected to a first lumen of the dual lumen catheter.

18. The foam generating apparatus according to claim 17, wherein the medical solution is fluidly connected to a second lumen of the dual lumen catheter.

19. The foam generating apparatus according to claim 18, wherein the foam generating tip assembly employs a Venturi arrangement with a mixing chamber.

20. The foam generating apparatus according to claim 15, wherein the compressed gas is pressurized $CO_2$.

21. A medical method, comprising:
treating arteries using the foam generating apparatus according to claim 15.

22. A medical method, comprising:
treating veins using the foam generating apparatus according to claim 15.

23. The medical method according to claim 22, wherein the vein is the great saphenous vein.

24. A gas enriched foam generating apparatus for performing medical procedures, comprising:
a foam generating tip assembly composed of a multi-channel arrangement at a proximal first end thereof and a tip at a distal second end thereof;
a compressed gas unit fluidly connected to the multi-channel arrangement at a proximal first end of the foam generating tip assembly; and
a medical solution fluidly connected to the multi-channel arrangement at a proximal first end of the foam generating tip assembly;
wherein compressed gas, from the compressed gas unit, and the medical solution are combined within the foam generating tip assembly in a manner generating a gas enriched foam that is ultimately dispensed from the foam generating apparatus; and
further including a needle body including the foam generating tip assembly wherein the compressed gas unit and the medical solution are fluidly connected to the multi-channel arrangement at a needle hub at a proximal end of the needle body.

25. The foam generating apparatus according to claim 24, wherein the multi-channel arrangement of the foam generating tip assembly employs a Venturi arrangement with a mixing chamber.

26. The foam generating apparatus according to claim 25, wherein the tip is composed of a material having a porous structure allowing for the passage of the pressurized gas and the medical solution.

27. The foam generating apparatus according to claim 24, wherein the compressed gas is pressurized $CO_2$.

28. A medical method, comprising:
treating arteries using the foam generating apparatus according to claim 24.

29. A medical method, comprising:
treating veins using the foam generating apparatus according to claim 24.

30. The medical method according to claim 29, wherein the vein is the great saphenous vein.

* * * * *